United States Patent
Ruland et al.

(10) Patent No.: US 7,335,235 B2
(45) Date of Patent: Feb. 26, 2008

(54) ALKOXYLATE MIXTURES AND DETERGENTS CONTAINING THE SAME

(75) Inventors: Alfred Ruland, Schriesheim (DE);
Martin Scholtissek, Wachenheim (DE);
Juergen Tropsch, Roemerberg (DE);
Richard Baur, Mutterstadt (DE)

(73) Assignee: BASF Akiengesellschaft, Ludwigshafen (DE)

( * ) Notice: Subject to any disclaimer, the term of this patent is extended or adjusted under 35 U.S.C. 154(b) by 398 days.

(21) Appl. No.: 10/511,445

(22) PCT Filed: Apr. 25, 2003

(86) PCT No.: PCT/EP03/04333

§ 371 (c)(1),
(2), (4) Date: Oct. 26, 2004

(87) PCT Pub. No.: WO03/091190

PCT Pub. Date: Nov. 6, 2003

(65) Prior Publication Data

US 2005/0170991 A1    Aug. 4, 2005

(30) Foreign Application Priority Data

Apr. 26, 2002    (DE) ............... 102 18 752
Sep. 18, 2002    (DE) ............... 102 43 361

(51) Int. Cl.
*C11D 1/72* (2006.01)
*C11D 1/825* (2006.01)
*C11D 3/37* (2006.01)
*D06L 1/12* (2006.01)

(52) U.S. Cl. .......... 8/137; 510/342; 510/360; 510/421; 510/475; 510/505

(58) Field of Classification Search .......... 510/342, 510/360, 421, 475, 505; 8/137
See application file for complete search history.

(56) References Cited

U.S. PATENT DOCUMENTS 2,508,036 A    5/1950  Kosmin
5,705,476 A  * 1/1998  Hoffarth .............. 510/535
6,482,972 B1 * 11/2002 Bahrmann et al. ...... 560/76

FOREIGN PATENT DOCUMENTS

| | | |
|---|---|---|
| DE | 24 48 532 | 4/1975 |
| DE | 42 37 178 | 5/1994 |
| DE | 101 17 273 | 10/2002 |
| EP | 0 616 026 | 9/1994 |
| WO | 91/09925 | 7/1991 |
| WO | 92/14808 | 9/1992 |
| WO | 93/18188 | 9/1993 |
| WO | 94/11330 | 5/1994 |
| WO | 94/11331 | 5/1994 |
| WO | 99/16775 | 4/1999 |
| WO | 01/77276 | 10/2001 |

OTHER PUBLICATIONS

Von Bernhard Wojtech, "Zur Darstellung hochmolekularer Polyäthylenoxyde," Aus dem Institut für Chemische Technologie der Technischen Hochschule München, May 14, 1963, pp. 180-194 (equivalent of B. Wojtech, Makromol. Chem. 66, (1966), p. 180).
Gee, Geoffrey et al. "The Polymerization of Epoxides. Part III. The Polymerization of Propylene Oxide by Sodium Alkoxides", J. Chem. Soc., pp. 4298-4303 1961.
Wojtech, Von Bernhard. "Zur Darstellung hochmelekularer Polyaethylenoxyde", Makromol. Chem., vol. 38, pp. 180-195, with English abstract 1960.

* cited by examiner

*Primary Examiner*—Brian Mruk
(74) *Attorney, Agent, or Firm*—Oblon, Spivak, McClelland, Maier & Neustadt, P.C.

(57) ABSTRACT

An alkoxylate mixture containing; at least one alkoxylate of the formula $C_nH_{2n+1}O(A)_x(B)_yH$ where A is ethyleneoxy, B is $C_3$-$C_{10}$-alkyleneoxy or mixtures thereof, n is an integer in the range from 8 to 11, x is a number in the range from 1 to 20, y is a number in the range from 0 to 10, and (ii) at least one alkoxylate of the formula $C_mH_{2m+1}O(A)_v(B)_wH$ where A is ethyleneoxy, B is $C_3$-$C_{10}$-alkyleneoxy or mixtures thereof, m is an integer in the range from 12 to 24, v is a number in the range from 1 to 50, w is a number in the range from 0 to 10.

8 Claims, No Drawings

ALKOXYLATE MIXTURES AND DETERGENTS CONTAINING THE SAME

The invention relates to alkoxylate mixtures and to detergents comprising these, and also to processes for the preparation of the alkoxylate mixtures and to the use of the detergent for the washing or cleaning of textiles.

For the purposes of this invention, detergents are usually used for the washing of materials of greater or lesser flexibility, preferably those which contain or consist of natural, synthetic or semisynthetic fiber materials and which consequently have at least partially a textile character.

Detergents of this type have been described widely in the prior art. A very good review of the mode of action and the composition of detergents is given, for example, in Ullmann's Encyclopedia of Industrial Chemistry, 5th edition, vol. A8, (1986), pages 315 ff, keyword "Detergents", and Tai, Formulating Detergents and Personal Care Products, AOCS Press, 2000. The detergents comprise a surfactant or two or more surfactants of the same or different surfactant groups and usually further auxiliaries and additives which are either required for formulation and/or which serve to adapt the detergents to the intended specific use purpose or the type of application (washing by hand or in machines). Constituents which can be used in many detergents in addition to the various surfactants in alternating combinations and proportions are, for example, builders (sequestering agents) and cobuilders, pH regulators, such as inorganic or organic acids, inorganic or organic bases and buffer systems, ion exchangers, dispersants, soil-carrying agents, thickeners, enzymes, bleaching systems, hydrotropic compounds as solubility promoters or solubilizers, such as, for example, urea or alcohols, foam regulators for stabilizing or suppressing foam, skin and corrosion protectants, disinfecting compounds or systems, for example those which comprise iodine or which release chlorine or hypochlorous acid, such as, for example, dichloroisocyanurate, perfume, dyes, optical (fluorescent) brighteners, graying inhibitors, extenders and formulating agents and disinfecting compounds. An essential part of the cleaning action of the detergents described in the prior art is due to the surfactants present therein. Surfactants which are used are ionic surfactants and, more specifically, both anionic surfactants, such as, for example, alcohol sulfates, alcohol ether sulfates, alkylbenzenesulfonates, α-olefinsulfonates, sulfosuccinates, and also cationic surfactants, such as, for example, $C_8$ to $C_{16}$-dialkyldimethylammonium salts, dialkoxydimethylammonium salts or imidazolinium salts with a long-chain alkyl radical.

The use of amphoteric surfactants, for example of derivatives of secondary or tertiary amines, such as, for example, $C_6$-$C_{18}$-alkylbetaines or $C_6$-$C_{15}$-alkylsulfobetaines or amine oxides, such as alkyldimethylamine oxides, has also already been described.

Nonionic surfactants, in particular also alkoxylates and polyglycosides of alkanols having, in particular, 8 to 20 carbon atoms, and alkoxylates of alkylamines and alkylamides are also used in detergents. In particular, it is also known to use alkoxylates of oxo alcohols having 10 to 13 carbon atoms as surfactants in detergents. DE-A-100 29 692 describes such alkoxylates.

In the interest of as sparing a use of materials as possible, good economic feasibility and low impact on the environment, the manufacturers of detergents strive for a continual improvement in the effectiveness of their products and in particular of the surfactants present therein.

It is an object of the present invention to provide alcohol alkoxylate surfactant systems which, in detergents and cleaners, lead to an improved removal of soil and improve the performance spectrum of the detergents and cleaners.

We have found that this object is achieved according to the invention by an alkoxylate mixture comprising
0.1 to 99.9% by weight of at least one alkoxylate of the formula (I)

$$C_nH_{2n+1}O(A)_x(B)_yH \quad (I)$$

where
A is ethyleneoxy,
B is $C_3$-$C_{10}$-alkyleneoxy, preferably propyleneoxy, butyleneoxy, pentyleneoxy or mixtures thereof,
where groups A and B may be present randomly distributed, alternately or in the form of two or more blocks in any order,
n is an integer in the range from 8 to 11,
x is a number in the range from 1 to 20,
y is a number in the range from 0 to 10, and
0.1 to 99.9% by weight of at least one alkoxylate of the formula (II)

$$C_mH_{2m+1}O(A)_v(B)_wH \quad (II)$$

where
A is ethyleneoxy,
B is $C_3$-$C_{10}$-alkyleneoxy, preferably propyleneoxy, butyleneoxy, pentyleneoxy or mixtures thereof,
where groups A and B may be present randomly distributed, alternately or in the form of two or more blocks in any order,
m is an integer in the range from 12 to 24,
v is a number in the range from 1 to 50,
w is a number in the range from 0 to 10.

According to the invention, it has been found that the alkoxylate mixtures derived from shorter-chain and longer-chain alkanols have a significantly improved washing behavior compared with known systems. The improvement is particularly marked compared with the use of exclusively short-chain alkanol ethoxylates. The use of such short-chain alkanol alkoxylates in detergent compositions is known per se.

WO 94/11331 relates to the use of alkoxylates of 2-propylheptanol in detergent compositions for degreasing hard surfaces. The alkoxylates have 2 to 16 alkylene oxide groups. The majority of the alkylene oxide groups is preferably in the form of ethylene oxide. According to the examples, exclusively ethoxylated alcohols are used. It is also described that the alcohols can be reacted firstly with ethylene oxide and then with propylene oxide. However, no examples or properties are given for such alkoxylates. It is stated that the alkoxylates described exhibit good detergency and wetting action, combined with low foaming. In addition, it is stated that the alkoxylates have a desired thickening effect in formulations.

WO 94/11330 relates to alkoxylates of 2-propylheptanol and to the use thereof. The alkoxylates contain 2-propylheptanol which has been reacted firstly with 1 to 6 mol of propylene oxide and then with 1 to 10 mol of ethylene oxide. According to the examples, a 2-propylheptanol reacted firstly with 4 mol of propylene oxide and then with 6 mol of ethylene oxide is used. It is stated that the alkylene oxide adducts exhibit an improved ratio of foaming behavior to detergency. It is also stated that the alkoxylates exhibit good wetting behavior. They are used in detergent compositions for the cleaning of textile materials.

U.S. Pat. No. 2,508,036 describes ethoxylates of 2-n-propylheptanol with 5 to 15 mol of ethylene oxide. It is stated that the alkoxylates exhibit improved wetting behavior in aqueous solutions and can therefore be used in detergents in combination with builders.

The text below describes in more detail the short-chain and the long-chain alkanol alkoxylate component of the alkoxylate mixtures according to the invention.

The mixtures according to the invention comprise 0.1 to 99% by weight, preferably 10 to 90% by weight, in particular 20 to 70% by weight, of at least one alkoxylate of the formula (I). Accordingly, they comprise 0.1 to 99% by weight, preferably 10 to 90% by weight, in particular 30 to 80% by weight, of at least one alkoxylate of the formula (II).

In the alkoxylate of the formula (I), A has the meaning ethyleneoxy. B is preferably propyleneoxy, butyleneoxy, pentyleneoxy or mixtures thereof, preferably propyleneoxy or butyleneoxy, in particular propyleneoxy.

n is an integer in the range from 8 to 11, n preferably has the value 10. These may be linear or branched alkyl radicals, it also being possible for mixtures of linear and branched alkyl radicals to be present. Particularly preferably, in the alkoxylate of the formula (I) in which n has the value 10, the radical $C_{10}H_{21}$ has the meaning $C_5H_{11}CH(C_3H_7)CH_2$. The shorter-chain alkoxylate is thus preferably derived from 2-propylheptanol, it also being possible for mixtures of isomers to be present.

For example, in the alkoxylate of the formula (I), 70 to 99% by weight, preferably 85 to 96% by weight of alkoxylates A1, in which $C_5H_{11}$ has the meaning n-$C_5H_{11}$, and 1 to 30% by weight, preferably 4 to 15% by weight of alkoxylates A2, in which $C_5H_{11}$ has the meaning $C_2H_5CH(CH_3)CH_2$ and/or $CH_3CH(CH_3)CH_2CH_2$, may be present in the mixture. Here, $C_3H_7$ preferably has the meaning n-$C_3H_7$.

The preparation of 2-propylheptanol(s) can take place starting from valeraldehyde by aldol condensation and subsequent hydrogenation. The preparation of valeraldehyde and the corresponding isomers takes place by hydroformylation of butene, as described, for example, in U.S. Pat. No. 4,287,370; Beilstein E IV 1, 3268, Ullmann's Encyclopedia of Industrial Chemistry, 5th edition, volume A1, pages 323 and 328f. The subsequent aldol condensation is described, for example, in U.S. Pat. No. 5,434,313. The hydrogenation of the aldol condensation product follows general hydrogenation conditions.

Furthermore, 2-propylheptanol can be prepared by condensation of 1-pentanol (as a mixture of the corresponding 1-methylbutanols) in the presence of KOH at elevated temperatures, see e.g. Marcel Guerbet, C. R. Acad. Sci., Paris, 128, 511, 1002 (1899). Furthermore, reference is made to Römpp, Chemie Lexikon, 9th edition, Georg Thieme Verlag, Stuttgart, and the citations given therein, and also to Tetrahedron 1967, Vol. 23, pages 1723-1733.

Suitable singly branched alkyl radicals are also 2-octyl-, 3-octyl- etc., 2-nonyl-, 3-nonyl -etc., 2-decyl-, 3-decyl- etc., 2-undecyl-, 3-undecyl- radicals etc. Appropriate alcohols can be prepared by addition of water to olefins, e.g. α-olefins.

Suitable multiply branched alkyl radicals comprise one or two, preferably one methyl- or ethyl substituent. One example is the (6-ethyl)-2-nonylradical. The appropriate alcohol is accessible by reaction of 2-ethyl hexanal and acetone followed by subsequent hydrogenation.

In the formula (I), x is a number in the range from 1 to 20, preferably 3 to 12. y is a number in the range from 0 to 10, preferably 0 to 5, particularly preferably 0. The values of x and y are average values since in the alkoxylation of alkanols a distribution of the degree of alkoxylation is usually obtained. For this reason, it is possible for x and y, like the v and w discussed below, to deviate from whole-number values. The distribution of the degree of alkoxylation can be adjusted to a certain extent through the use of different alkoxylation catalysts. If, in addition to ethylene oxide, one or more longer-chain alkylene oxides are used for the alkoxylation, then the different alkylene oxide radicals can be present in random distribution, alternately or in the form of two or more blocks in any order. The alkoxylation is particularly preferably only carried out with ethylene oxide so that a pure (poly)ethylene oxide radical is present. The average value of the homolog distribution is represented by the given numbers x and y.

In the longer-chain alkoxylate of the formula (II), A and B preferably have the above meaning. m is an integer in the range from 12 to 24, preferably from 12 to 18, particularly preferably from 12 to 15. The alkyl radical $C_mH_{2m+1}$ may here be linear or branched. It is also possible for mixtures of linear and branched alkyl radicals to be present. They can originate from any suitable sources. The linear alcohols are of native or synthetic origin. Among the branched alcohols mention is to be made of the following examples:

oxo alcohols based on linear or branched olefins,
secondary alcohols, obtained for example by paraffin oxidation,
alcohols obtained by the SHOP process,
alcohols obtainable via GTL technology,
alcohols obtainable via Fischer-Tropsch technology,
alcohols obtainable via backbone isomerization of the olefins used for the hydroformylation, in accordance with WO 98/23566.

Appropriate alcohols, which are branched, show the hydroxy group e. g. in 2-, 3-, 4-position. The alkyl radical may be linear or further branched and may show e. g. methyl- or ethyl substituents.

Examples of appropriate alcohols are 2-dodecyl alcohol, 2-tetradecyl alcohol, 2-hexadecyl alcohol, in each case accessible by addition of water to α-olefins, (7-ethyl)-3-decyl alcohol, respectively (3-methyl-6-ethyl)-2-nonylalcohol, accessible by reaction of 2-ethyl hexanal and methyl ethyl ketone followed by subsequent hydrogenation, 2-hexadecyl alcohol, respectively 2-octadecyl alcohol, accessible by reaction of $C_{13}/C_{15}$-aldehyde and acetone, 3-nonadecyl alcohol, respectively (3-methyl)-2-octadecyl alcohol, (3-methyl)-2-hexadecyl alcohol, 3-heptadecyl alcohol, accessible by reaction of $C_{13}/C_{13}$-aldehyde and methyl ethyl ketone. The reaction products based on $C_{13}/C_{15}$-aldehyde are branched at about 40-50% in the alpha-position in the chemical mixtures.

Further examples for appropriate alcohols are linear $C_{12-14}$-alkanes showing a hydroxy group in a non terminal position of the carbon chain, respectively mixtures thereof (e. g. Softanol®-alcohols of Nippon Shokubai or Tergitol®-alcohols of Dow).

v is a number in the range from 1 to 50, preferably from 3 to 15. b is a number in the range from 0 to 10, preferably in the range from 0 to 5. In particular, w has the value 0. Reference may be made to the above statements regarding x and y in the case of the shorter-chain alcohol alkoxylates.

The invention further provides a process for the preparation of alkoxylate mixtures as described above, in which alkanols of the formula $C_nH_{2n+1}OH$ and $C_mH_{2m+1}OH$ with the given meaning for n and m are reacted with $C_{2-5}$-alkylene oxides ander alkoxylation conditions and are mixed together before or after alkoxylation or after partial alkoxylation.

The alkoxylation can be carried out, for example, using alkaline catalysts, such as alkali metal hydroxides or alkali metal alkoxides. The use of these catalysts results in special properties, in particular the distribution of the degree of alkoxylation.

The alkoxylation can additionally be carried out using Lewis-acidic catalysis with the special properties resulting therefrom, in particular in the presence of $BF_3 \times H_3PO_4$, $BF_3$ dietherate, $SbCl_5$, $SnCl_4 \times 2\ H_2O$, hydrotalcite. Suitable as catalyst are also double metal cyanimide compounds (DMC).

In this process, the excess alcohol can be distilled off, or the alkoxylate can be obtained by a two-stage process. The preparation of mixed alkoxylates from, for example, EO and PO is also possible, in which case firstly a polyethylene oxide block can join to the alkanol radical, followed by an ethylene oxide block, or firstly an ethylene oxide block and then a propylene oxide block. Random distributions are also possible. Preferred reaction conditions are given below.

The alkoxylation is preferably catalyzed by strong bases, which are expediently added in the form of an alkali metal hydroxide or alkaline earth metal hydroxide, usually in an amount of from 0.1 to 1% by weight, based on the amount of the alkanol $R^2$—OH. (Cf. G. Gee et al., J. Chem. Soc. (1961), p. 1345; B. Wojtech, Makromol. Chem. 66, (1966), p. 180.)

An acidic catalysis of the addition reaction is also possible. In addition to Bronsted acids, Lewis acids are also suitable, such as, for example, $AlCl_3$ or $BF_3$. (Cf. P. H. Plesch, The Chemistry of Cationic Polymerization, Pergamon Press, New York (1963).

In principle, all suitable compounds known to a person skilled in the art may be used as a DMC compound.

DMC compounds suitable as a catalyst are described, for example, in WO 99/16775 and in DE 10117273.7. The following are particularly suitable as a catalyst for the alkoxylation of a double metal cyanide compound of the formula I:

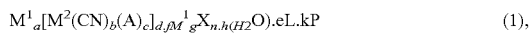

$$M^1{}_a[M^2(CN)_b(A)_c]_{d}f M^1{}_g X_{n \cdot h(H_2O)} \cdot eL \cdot kP \qquad (1),$$

where
- $M^1$ is at least one metal ion selected from the group consisting of $Zn^{2+}$, $Fe^{2+}$, $Fe^{3+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W^{4+}$, $W^{6+}$, $Cr^{2+}$, $Cr^{3+}$, $Cd^{2+}$, $Hg^{2+}$, $Pd^{2+}$, $Pt^{2+}$, $V^{2+}$, $Mg^{2+}$, $Ca^{2+}$, $Ba^{2+}$, $Cu^{2+}$, $La^{3+}$, $Ce^{3+}$, $Ce^{4+}$, $Eu^{3+}$, $Ti^{3+}$, $Ti^{4+}$, $Ag^+$, $Rh^{2+}$, $Rh^{3+}$, $Ru^{2+}$ and $Ru^{3+}$,
- $M^2$ is at least one metal ion selected from the group consisting of $Fe^{2+}$, $Fe^{3+}$, $Co^{2+}$, $Co^{3+}$, $Mn^{2+}$, $Mn^{3+}$, $V^{4+}$, $V^{5+}$, $Cr^{2+}$, $Cr^{3+}$, $Rh^{3+}$, $Ru^{2+}$ and $Ir^{3+}$,
- A and X, independently of one another, are each an anion selected from the group consisting of halide, hydroxide, sulfate, carbonate, cyanide, thiocyanate, isocyanate, cyanate, carboxylate, oxalate, nitrate, nitrosyl, hydrogen sulfate, phosphate, dihydrogen phosphate, hydrogen phosphate and bicarbonate,
- L is a water-miscible ligand selected from the group consisting of alcohols, aldehydes, ketones, ethers, polyethers, esters, polyesters, polycarbonate, ureas, amides, primary, secondary and tertiary amines, ligands having pyridine nitrogen, nitriles, sulfides, phosphides, phosphites, phosphines, phosphonates and phosphates,
- k is a fraction or integer greater than or equal to zero and P is an organic additive,
- a, b, c, d, g and n are selected so that the electroneutrality of the compound (I) is ensured, it being possible for c to be 0,
- e is the number of ligand molecules and is a fraction or integer greater than 0 or 0,
- f, h and m, independently of one another, are a fraction or integer greater than 0 or 0.

Examples of organic additives P are: polyether, polyester, polycarbonates, polyalkylene glycol sorbitan ester, polyalkylene glycol glycidyl ether, polyacrylamide, poly(acrylamide-co-acrylic acid), polyacrylic acid, poly(acrylamide-co-maleic acid), polyacrylonitrile, polyalkylene acrylates, polyalkyl methacrylates, polyvinyl methyl ether, polyvinyl ethyl ether, polyvinyl acetate, polyvinyl alcohol, poly-N-vinylpyrrolidone, poly(N-vinylpyrrolidone-co-acrylic acid), polyvinyl methyl ketone, poly(4-vinylphenol), poly(acrylic acid-co-styrene), oxazoline polymers, polyalkylenimines, maleic acid and maleic anhydride copolymers, hydroxyethylcellulose, polyacetates, ionic surface-active and interface-active compounds, gallic acid or salts, esters or amides thereof, carboxylic esters of polyhydric alcohols and glycosides.

These catalysts may be crystalline or amorphous. Where k is zero, crystalline double metal cyanide compounds are preferred. Where k is greater than zero, crystalline, semicrystalline and substantially amorphous catalysts are preferred.

There are various preferred embodiments of the modified catalysts. A preferred embodiment comprises catalysts of the formula (I) in which k is greater than zero. The preferred catalyst then contains at least one double metal cyanide compound, at least one organic ligand and at least one organic additive P.

In another preferred embodiment, k is zero, e is optionally also zero and X is exclusively a carboxylate, preferably formate, acetate or propionate. Such catalysts are described in WO 99/16775. In this embodiment, crystalline double metal cyanide catalysts are preferred. Furthermore, double metal cyanide catalysts as described in WO 00/74845, which are crystalline or lamellar, are preferred.

The modified catalysts are prepared by combining a metal salt solution with a cyanometallate solution, which solution may optionally contain both an organic ligand L and an organic additive P. The organic ligand and optionally the organic additive are then added. In a preferred embodiment of the catalyst preparation, an inactive double metal cyanide phase is first prepared and this is then converted into an active double metal cyanide phase by recrystallization, as described in PCT/EP01/01893.

In another preferred embodiment of the catalysts, f, e and k are not zero. These are double metal cyanide catalysts which contain a water-miscible organic ligand (in general in amounts of from 0.5 to 30% by weight) and an organic additive (in general in amounts of from 5 to 80% by weight), as described in WO 98/06312. The catalysts can be prepared either with vigorous stirring (24 000 rpm using a Turrax) or with stirring, as described in U.S. Pat. No. 5,158,922.

Double metal cyanide compounds which contain zinc, cobalt or iron or two thereof are particularly suitable as a catalyst for the alkoxylation. For example, Prussian blue is particularly suitable.

Crystalline DMC compounds are preferably used. In a preferred embodiment, a crystalline DMC compound of the Zn—Co type which contains zinc acetate as a further metal salt component is used. Such compounds crystallize in a monoclinic structure and have a lamellar habit. Such compounds are described, for example, in WO 00/74845 or PCT/EP01/01893.

DMC compounds suitable as a catalyst can in principle be prepared by all methods known to a person skilled in the art. For example, the DMC compounds can be prepared by direct precipitation, the incipient wetness method, by preparation of a precursor phase and subsequent recrystallization.

The DMC compounds can be used in the form of a powder, paste or suspension or can be shaped to give a molding, introduced into moldings, foams or the like or applied to moldings, foams or the like.

The catalyst concentration used for the alkoxylation, based on the final quantity range, is typically less than 2 000 ppm, preferably less than 1 000 ppm, in particular less than 500 ppm, particularly preferably less than 100 ppm, for example less than 50 ppm.

The addition reaction is carried out at temperatures of from about 90 to about 240° C., preferably from 120 to 180° C., in a closed vessel. The alkylene oxide or the mixture of different alkylene oxides is added to the mixture of alkanol mixture according to the invention and alkali ander the vapor pressure of the alkylene oxide mixture which prevails at the chosen reaction temperature. If desired, the alkylene oxide can be diluted by up to 30 to 60% with an inert gas. This ensures additional safety against explosion-like polyaddition of the alkylene oxide.

If an alkylene oxide mixture is used, then polyether chains are formed in which the various alkylene oxide building blocks are distributed in a virtually random manner. Variations in the distribution of the building blocks along the polyether chain arise as a result of different rates of reaction of the components and can also be achieved voluntarily through the continuous introduction of an alkylene oxide mixture of program-controlled composition. If the different alkylene oxides are reacted one after the other, polyether chains are obtained which have a block-like distribution of the alkylene oxide building blocks.

The length of the polyether chains varies within the reaction product statistically about an average value which essentially corresponds to the stoichiometric value which arises from the amount added.

The alkoxylate mixtures according to the invention are preferably used in detergents or cleaners, where they lead to an improvement in the washing properties. The invention also provides a detergent or cleaner comprising an alkoxylate mixture as described above. The alkoxylate mixture is here customarily used in an amount of from 0.01 to 80% by weight, preferably in an amount of from 0.01 to 50% by weight, based on the detergent or cleaner. The detergent or cleaner is preferably used for the washing or cleaning of textiles.

The minimum proportion of the alkoxylate mixtures according to the invention of the overall weight of the detergents according to the invention is measured so that a significant effect of this addition arises. Good detergency, in particular very good primary detergency, of the detergents according to the invention is generally achieved if the proportion of the mixtures in the detergent according to the invention, based on the total weight of the composition, is 0.01 to 50% by weight, preferably 0.1 to 40% by weight, in particular 0.5 to 30% by weight.

For the purposes of this invention, detergents are generally used for the washing of materials of greater or lesser flexibility, preferably those which contain or consist of natural, synthetic or semisynthetic fiber materials and which consequently usually have at least partially a textile character. The materials which contain or consist of fibers can, in principle, be in any form which exists in use or for the preparation and processing. For example, fibers may be unarranged in the form of staple or aggregate, arranged in the form of threads, yarns, twines, or in the form of fabrics, such as nonwovens, loden materials or felt, wovens, knits in all conceivable types of weave.

These may be raw fibers or fibers in any stages of processing and may be natural protein or cellulose fibers, such as wool, silk, cotton, sisal, hemp, coconut fibers or synthetic fibers, such as, for example, polyester, polyamide or polyacrylonitrile fibers.

The detergents according to the invention can also be used for cleaning fiber-containing materials, such as e.g. backed carpets with cut or uncut pile.

The compositions of the detergents are preferably adapted to the different purposes, as is familiar to the person skilled in the art from the prior art. For this purpose, all auxiliaries and additives corresponding to the purpose and known from the prior art can be added to the detergents according to the invention.

In addition to the mixtures according to the invention, the following may, for example, be present in detergents:

builders and cobuilders, such as polyphosphates, zeolites, polycarboxylates, phosphonates or complexing agents ionic surfactants, such as alcohol sulfates/ether sulfates, alkylbenzenesulfonates, $\alpha$-olefinsulfonates and other alcohol sulfates/ether sulfates other nonionic surfactants, such as alkylamine alkoxyates, alkyl polyglucosides optical brighteners color transfer inhibitors, such as polyvinylpyrrolidone of molar masses 8000 to 70 000, vinylimidazole/vinylpyrrolidone copolymers with a molar ratio of the monomers of from 1:10 to 2:1 and molar masses of from 8000 to 70 000, and poly-4-vinylpyridine N-oxides with molar masses of from 8000 to 70 000 extenders, such as sodium sulfate or magnesium sulfate soil release agent incrustation inhibitors bleaching systems, comprising bleach, such as perborate, percarbonate and bleach activators, such as tetraacetylethylenediamine, and also bleach stabilizers perfume (oils)

foam suppressors, such as silicone oils enzymes, such as amylases, lipases, cellulases, proteases alkali metal donors, such as soluble alkali metal silicates, e.g. pentasodium methasilicate, sodium carbonate.

Solvents, such as ethanol, isopropanol, 1,2-propylene glycol, butyl glycol etc., can, for example, additionally be used in liquid detergents.

In tablet detergents, it is additionally possible to use tableting auxiliaries, such as polyethylene glycols with molar masses of more than 1000 g/mol, polymer dispersions, and tablet disintegrants, such as cellulose derivatives, crosslinked polyvinylpyrrolidone, crosslinked polyacrylates or combinations of acids, such as citric acid and sodium bicarbonate. A detailed list of possible ingredients is given below.

In some cases, it may be expedient to combine the mixtures used according to the invention with other nonionic surfactants, such as alkylamine alkoxylates, alkylamide alkoxylates, alkyl polyglucosides, or with ionic, preferably anionic, surfactants, such as, for example, alcohol sulfate/ether sulfates, alkylbenzenesulfonates, $\alpha$-olefinsulfonates, sulfosuccinates, or with amphoteric surfactants, such as, for example, alkylamine oxides, or betaines.

Examples of surfactants of varying nature suitable for the combination are given below:

A class of suitable nonionic surfactants are alkylphenol alkoxylates, such as alkylphenol ethoxylates having $C_6$ to $C_{14}$-alkyl chains and 5 to 30 mol of alkylene oxide units.

Another class of nonionic surfactants are alkyl polyglucosides having 6 to 22, preferably 10 to 18, carbon atoms in the alkyl chain. These compounds generally contain 1 to 20, preferably 1.1 to 5, glucoside units.

Another class of nonionic surfactants are N-alkylglucamides of the structures

where $B^1$ is a $C_6$- to $C_{22}$-alkyl, $B^2$ is hydrogen or $C_1$- to $C_4$-alkyl and D is a polyhydroxyalkyl radical having 5 to 12 carbon atoms and at least 3 hydroxyl groups. Preferably, $B^1$ is $C_{10}$- to $C_{18}$-alkyl, $B^2$ is $CH_3$ and D is a $C_5$- or $C_6$-radical. For example, such compounds are obtained by the acylation of reductively aminated sugars with acid chlorides of $C_{10}$- to $C_{18}$-carboxylic acids.

Further suitable nonionic surfactants are the terminally capped fatty acid amide alkoxylates, known from WO-A 95/11225, of the formula

in which
$R^1$ is a $C_5$- to $C_{21}$-alkyl or alkenyl radical,
$R^2$ is a $C_1$- to $C_4$-alkyl group,
$A^1$ is $C_2$- to $C_4$-alkylene,
y is the number 2 or 3 and
x has a value from 1 to 6.

Examples of such compounds are the reaction products of n-butyltriglycolamine of the formula $H_2N-(CH_2-CH_2-O)_3-C_4H_9$ with methyl dodecanoate or the reaction products of ethyltetraglycolamine of the formula $H_2N-(CH_2-CH_2-O)_4-C_2H_5$ with a standard commercial mixture of saturated $C_8$- to $C_{18}$-fatty acid methyl esters.

Further suitable nonionic surfactants are also block copolymers of ethylene oxide, propylene oxide and/or butylene oxide (Pluronic® and Tetronic® brands from BASF), polyhydroxy or polyalkoxy fatty acid derivatives, such as polyhydroxy fatty acid amides, N-alkoxy- or N-aryloxy-polyhydroxy fatty acid amides, fatty acid amide ethoxylates, in particular terminally capped ones, and fatty acid alkanolamide alkoxylates.

The additional nonionic surfactants are present in the detergents according to the invention preferably in an amount of from 0.01 to 30% by weight, in particular 0.1 to 25% by weight, especially 0.5 to 20% by weight.

It is also possible to use individual nonionic surfactants or a combination of different nonionic surfactants. The nonionic surfactants used may come from only one class, in particular only alkoxylated $C_8$- to $C_{22}$-alcohols, or surfactant mixtures from different classes can be used.

Suitable anionic surfactants are, for example, fatty alcohol sulfates of fatty alcohols having 8 to 22, preferably 10 to 18, carbon atoms, $C_{12}$-$C_{18}$-alcohol sulfates, lauryl sulfate, cetyl sulfate, myristyl sulfate, palmityl sulfate, stearyl sulfate and tallow fatty alcohol sulfate.

Further suitable anionic surfactants are sulfated ethoxylated $C_8$- to $C_{22}$-alcohols (alkyl ether sulfates) or soluble salts thereof. Compounds of this type are prepared, for example, by firstly alkoxylating a $C_8$- to $C_{22}$-, preferably a $C_{10}$- to $C_{18}$-alcohol, e.g. a fatty alcohol, and then sulfating the alkoxylation product. For the alkoxylation, preference is given to using ethylene oxide, 1 to 50 mol, preferably 1 to 20 mol, of ethylene oxide being used per mole of alcohol. The alkoxylation of the alcohols can, however, also be carried out with propylene oxide on its own and optionally butylene oxide. Furthermore, also suitable are those alkylated $C_8$- to $C_{22}$-alcohols which contain ethylene oxide and propylene oxide or ethylene oxide and butylene oxide or ethylene oxide and propylene oxide and butylene oxide. The alkoxylated $C_8$- to $C_{22}$-alcohols can contain the ethylene oxide, propylene oxide and butylene oxide units in the form of blocks or in random distribution. Depending on the nature of the alkoxylation catalyst, alkyl ether sulfates can be obtained with a broad or narrow alkane oxide homolog distribution.

Further suitable anionic surfactants are alkanesulfonates, such as $C_8$- to $C_{24}$-, preferably $C_{10}$- to $C_{18}$-alkanesulfonates, and soaps, such as, for example, the Na and K salts of saturated and/or unsaturated $C_8$- to $C_{24}$-carboxylic acids.

Further suitable anionic surfactants are linear $C_8$- to $C_{20}$-alkylbenzenesulfonates ("LAS"), preferably linear $C_9$- to $C_{13}$-alkylbenzenesulfonates and -alkyltoluenesulfonates.

Further suitable anionic surfactants are also $C_8$- to $C_{24}$-olefinsulfonates and -disulfonates, which may also represent mixtures of alklene- and hydroxyalkanesulfonates or -disulfonates, alkyl ester sulfonates, sulfonated polycarboxylic acids, alkylglycerol sulfonates, fatty acid glycerol ester sulfonates, alkylphenol polyglycol ether sulfates, paraffinsulfonates having about 20 to about 50 carbon atoms (based on paraffin or paraffin mixtures obtained from natural sources), alkyl phosphates, acyl isethionates, acyl taurates, acyl methyltaurates, alkylsuccinic acids, alkenylsuccinic acids or half-esters or half-amides thereof, alkylsulfosuccinic acids or amides thereof, mono- and diesters of sulfosuccinic acids, acyl sarcosinates, sulfated alkyl polyglucosides, alkyl polyglycol carboxylates and hydroxyalkyl sarcosinates.

The anionic surfactants are preferably added to the detergent in the form of salts. Suitable cations in these salts are alkali metal ions, such as sodium, potassium and lithium and ammonium salts, such as, e.g. hydroxyethylammonium, di(hydroxyethyl)ammonium and tri(hydroxyethyl)ammonium salts.

The anionic surfactants are present in the detergents according to the invention preferably in an amount of up to 30% by weight, for example from 0.1 to 30% by weight, especially 1 to 25% by weight, in particular 3 to 20% by weight. If $C_9$- to $C_{20}$ linear alkyl-benzenesulfonates (LAS) are co-used, these are usually employed in an amount up to 15% by weight, in particular up to 10% by weight.

It is possible to use individual anionic surfactants or a combination of different anionic surfactants. The anionic surfactants used may be from only one class, for example only fatty alcohol sulfates or only alkylbenzenesulfonates, although it is also possible to use surfactant mixtures from different classes, e.g. a mixture of fatty alcohol sulfates and alkylbenzenesulfonates.

In addition, the surfactant mixtures to be used according to the invention can be combined with cationic surfactants, customarily in an amount up to 25% by weight, preferably 1 to 15% by weight, for example $C_8$- to $C_{16}$-dialkyldimethylammonium salts, dialkoxydimethylammonium salts or imidazolinium salts with a long-chain alkyl radical; and/or with amphoteric surfactants, customarily in an amount up to 15% by weight, preferably 1 to 10% by weight, for example derivatives of secondary or tertiary amines, such as, e.g. $C_6$-$C_{18}$-alkylbetaines or $C_6$-$C_{15}$-alkylsulfobetaines or alkylamidobetaines or amine oxides, such as alkyldimethylamine oxides.

It is also possible to use cationic surfactants as are described in WO 99/19435.

The mixtures to be used according to the invention are usually combined with builders (sequestering agents), such as, for example, polyphosphates, polycarboxylates, phosphonates, complexing agents, e.g. methylglycinediacetic acid and salts thereof, nitrilotriacetic acid and salts thereof, ethylenediaminetetraacetic acid and salts thereof, and optionally with cobuilders.

Individual builder substances which are highly suitable for the combination with the mixtures to be used according to the invention may be listed below:

Suitable inorganic builders are primarily crystalline or amorphous alumosilicates having ion-exchanging properties, such as, in particular, zeolites. Various types of zeolites are suitable, in particular zeolites A, X, B, P, MAP and HS in their Na form or in forms in which Na is partially replaced by other cations, such as Li, K, Ca, Mg or ammonium. Suitable zeolites are described, for example, in U.S. Pat. No. 4,604,224.

Examples of crystalline silicates which are suitable as builders are disilicates or phyllosilicates, e.g. $\delta$-$Na_2Si_2O_5$ or $\beta$-$Na_2Si_2O_5$. The silicates can be used in the form of their alkali metal, alkaline earth metal or ammonium salts, preferably as Na, Li and Mg silicates. Amorphous silicates, such as, for example, sodium metasilicate, which has a polymeric structure, or amorphous disilicate can likewise be used.

Suitable carbonate-based inorganic builder substances are carbonates and hydrogencarbonates. These can be used in the form of their alkali metal, alkaline earth metal or ammonium salts. Preference is given to using Na, Li and Mg carbonates or hydrogencarbonates, in particular sodium carbonate and/or sodium hydrogencarbonate.

Customary phosphates used as inorganic builders are alkali metal orthophosphates and/or polyphosphates, such as, for example, pentasodium triphosphate. Said builder components can be used individually or in mixtures with one another.

In addition, in many cases, it is expedient to add cobuilders to the detergents according to the invention. Examples of suitable substances are listed below:

In a preferred embodiment, the detergents according to the invention comprise, in addition to the inorganic builders, 0.05 to 20% by weight, in particular 1 to 10% by weight, of organic cobuilders in the form of low molecular weight, oligomeric or polymeric carboxylic acids, in particular polycarboxylic acids, or phosphonic acids or salts thereof, in particular Na or K salts.

Low molecular weight carboxylic acids or phosphonic acids suitable as organic cobuilders are, for example, phosphonic acids, such as, for example, 1-hydroxyethane-1,1-diphosphonic acid, amino-tris(methylenephosphonic acid), ethylenediaminetetra(methylenephosphonic acid), hexamethylenediaminetetra(methylenephosphonic acid) and diethylenetriaminepenta-(methylenephosphonic acid);

$C_4$- to $C_{20}$-di-, -tri- and -tetracarboxylic acids, such as, for example, succinic acid, propanetricarboxylic acid, butanetetracarboxylic acid, cyclopentanetetracarboxylic acid and alkyl- and alkenylsuccinic acids having $C_2$- to $C_{16}$-alkyl- or -alkenyl radicals;

$C_4$- to $C_{20}$-hydroxycarboxylic acids, such as, for example, malic acid and tartaric acid;

gluconic acid, glutaric acid, citric acid, lactobionic acid and sucrose mono-, di- and tricarboxylic acid;

aminopolycarboxylic acids, such as, for example, nitrilotriacetic acid, $\beta$-alaninediacetic acid, ethylenediaminetetraacetic acid, serinediacetic acid, isoserinediacetic acid, alkylethylenediaminetriacetates, N,N-bis(carboxymethyl) glutamic acid, ethylenediaminedisuccinic acid and N-(2-hydroxyethyl)iminodiacetic acid, methyl- and ethylglycinediacetic acid.

Examples of oligomeric or polymeric carboxylic acids which are suitable as organic cobuilders are:

oligomaleic acids, as are described, for example, in EP-A 451508 and EP-A 396303;

co- and terpolymers of unsaturated $C_4$- to $C_8$-dicarboxylic acids, the copolymerized comonomers being monoethylenically unsaturated monomers from group (i), given below, in amounts of up to 95% by weight, from group (ii) in amounts of up to 60% by weight and from group (iii) in amounts of up to 20% by weight.

Examples of unsaturated $C_4$- to $C_8$-dicarboxylic acids in this context are maleic acid, fumaric acid, itaconic acid and citraconic acid. Preference is given to maleic acid.

Group (i) includes monoethylenically unsaturated $C_3$-$C_8$-monocarboxylic acids, such as, for example, acrylic acid, methacrylic acid, crotonic acid and vinylacetic acid. From group (i), preference is given to using acrylic acid and methacrylic acid.

Group (ii) includes monoethylenically unsaturated $C_2$- to $C_{22}$-olefins, vinyl alkyl ethers having $C_1$- to $C_8$-alkyl groups, styrene, vinyl esters of $C_1$- to $C_8$-carboxylic acids, (meth) acrylamide and vinylpyrrolidone. From group (ii), preference is given to using $C_2$- to $C_6$-olefins, vinyl alkyl ethers having $C_1$- to $C_4$-alkyl groups, vinyl acetate and vinyl propionate.

If the polymers of group (ii) contain copolymerized vinyl esters, some or all of the latter can also be present in hydrolyzed form to give vinyl alcohol structural units. Suitable co- and terpolymers are known, for example, from U.S. Pat. No. 3,887,806 and DE-A 4313909.

Group (iii) includes (meth)acrylic esters of $C_1$- to $C_8$-alcohols, (meth)acrylonitrile, (meth)acrylamides of $C_1$- to $C_8$-amines, N-vinylformamide and N-vinylimidazole.

Also suitable as organic cobuilders are homopolymers of monoethylenically unsaturated $C_3$-$C_8$-monocarboxylic acids, such as, for example, acrylic acid, methacrylic acid, crotonic acid and vinylacetic acid, in particular acrylic acid and methacrylic acid;

copolymers of dicarboxylic acids, such as, for example, copolymers of maleic acid and acrylic acid in the weight ratio 10:90 to 95:5, particularly preferably those in the weight ratio 30:70 to 90:10 with molar masses of from 1000 to 150 000;

terpolymers of maleic acid, acrylic acid and a vinyl ester of a $C_1$-$C_3$-carboxylic acid in the weight ratio 10 (maleic acid):90 (acrylic acid+vinyl ester) to 95 (maleic acid):10 (acrylic acid+vinyl ester), where the weight ratio of acrylic acid to the vinyl ester can vary within the range from 30:70 to 70:30;

copolymers of maleic acid with $C_2$-$C_8$-olefins in the molar ratio 40:60 to 80:20, copolymers of maleic acid with ethylene, propylene or isobutene in the molar ratio 50:50 being particularly preferred.

Graft polymers of unsaturated carboxylic acids onto low molecular weight carbohydrates or hydrogenated carbohydrates, cf. U.S. Pat. No. 5,227,446, DE-A 4415623 and DE-A 4313909, are likewise suitable as organic cobuilders.

Examples of suitable unsaturated carboxylic acids in this context are maleic acid, fumaric acid, itaconic acid, citraconic acid, acrylic acid, methacrylic acid, crotonic acid and vinylacetic acid, and also mixtures of acrylic acid and maleic acid which are grafted on in amounts of from 40 to 95% by weight, based on the component to be grafted.

For modification, it is additionally possible for up to 30% by weight, based on the component to be grafted, of further monoethylenically unsaturated monomers to be present in copolymerized form. Suitable modifying monomers are the abovementioned monomers of groups (ii) and (iii).

Suitable graft bases are degraded polysaccharides, such as, for example, acidically or enzymatically degraded starches, inulins or cellulose, protein hydrolyzates and reduced (hydrogenated or reductively aminated) degraded polysaccharides, such as, for example, mannitol, sorbitol, aminosorbitol and N-alkylglucamine, and also polyalkylene glycols with molar masses up to $M_w=5000$, such as, for example, polyethylene glycols, ethylene oxide/propylene oxide or ethylene oxide/butylene oxide or ethylene oxide/propylene oxide/butylene oxide block copolymers and alkoxylated mono- or polyhydric $C_1$- to $C_{22}$-alcohols (cf. U.S. Pat. No. 5,756,456).

Polyglyoxylic acids suitable as organic cobuilders are described, for example, in EP-B-001004, U.S. Pat. No. 5,399,286, DE-A-4106355 and EP-A-656914. The end groups of the polyglyoxylic acids may have different structures.

Polyamidocarboxylic acids and modified polyamidocarboxylic acids suitable as organic cobuilders are known, for example, from EP-A-454126, EP-B-511037, WO-A-94/01486 and EP-A-581452.

In particular, polyaspartic acids or cocondensates of aspartic acid with further amino acids, $C_4$- to $C_{25}$-mono- or -dicarboxylic acids and/or $C_4$- to $C_{25}$-mono- or -diamines are also used as organic cobuilders. Particular preference is given to using polyaspartic acids which have been prepared in phosphorus-containing acids and modified with $C_6$- to $C_{22}$-mono- or -dicarboxylic acids or with $C_6$- to $C_{22}$-mono- or -diamines.

Also suitable as organic cobuilders are iminodisuccinic acid, oxydisuccinic acid, aminopolycarboxylates, alkylpolyaminocarboxylates, aminopolyalkylenephosphonates, polyglutamates, hydrophobically modified citric acid, such as, for example, agaric acid, poly-α-hydroxyacrylic acid, N-acylethylenediaminetriacetates, such as lauroyl ethylenediaminetriacetate and alkylamides of ethylenediaminetetraacetic acid, such as EDTA-tallow amide.

Furthermore, it is also possible to use oxidized starches as organic cobuilders.

Further suitable (co)builders are described in WO 99/19435.

In a further preferred embodiment, the detergents according to the invention additionally comprise, in particular in addition to the inorganic builders, the anionic surfactants and/or the nonionic surfactants, 0.5 to 20% by weight, in particular 1 to 10% by weight, of glycine-N,N-diacetic acid derivatives, as described in WO 97/19159.

It is also frequently expedient to add bleaching systems, consisting of bleaches, such as, for example, perborate, percarbonate, and optionally bleach activators, such as, for example, tetraacetylethylenediamine,+bleach stabilizers and optionally bleach catalysts to the detergents according to the invention.

In these cases, the detergents according to the invention additionally comprise 0.5 to 30% by weight, in particular 5 to 27% by weight, especially 10 to 23% by weight, of bleaches in the form of percarboxylic acids, e.g. diperoxododecanedicarboxylic acid, phthalimidopercaproic acid, or monoperoxophthalic acid or -terephthalic acid, adducts of hydrogen peroxide with inorganic salts, e.g. sodium perborate monohydrate, sodium perborate tetrahydrate, sodium carbonate perhydrate or sodium phosphate perhydrate, adducts of hydrogen peroxide with organic compoands, e.g. urea perhydrate, or of inorganic peroxo salts, e.g. alkali metal persulfates or peroxodisulfates, optionally in combination with 0 to 15% by weight, preferably 0.1 to 15% by weight, in particular 0.5 to 8% by weight, of bleach activators.

Suitable bleach activators are:

polyacylated sugars, e.g. pentaacetylglucose;

acyloxybenzenesulfonic acids and alkali metal and alkaline earth metal salts thereof, e.g. sodium p-nonanoyloxybenzenesulfonate or sodium p-benzoyloxybenzene-sulfonate;

N,N-diacylated and N,N,N',N'-tetraacylated amines, e.g. N,N,N',N'-tetraacetyl-methylenediamine and -ethylenediamine (TAED), N,N-diacetylaniline, N,N-diacetyl-p-toluidine or 1,3-diacylated hydantoins, such as 1,3-diacetyl-5,5-dimethylhydantoin;

N-alkyl-N-sulfonylcarbonamides, e.g. N-methyl-N-mesylacetamide or N-methyl-N-mesylbenzamide;

N-acylated cyclic hydrazides, acylated triazoles or urazoles, e.g. monoacetylmaleic hydrazide;

O,N,N-trisubstituted hydroxylamines, e.g. O-benzoyl-N,N-succinylhydroxylamine, O-acetyl-N,N-succinylhydroxylamine or O,N,N-triacetylhydroxylamine;

N,N'-diacylsulfurylamides, e.g. N,N'-dimethyl-N,N'-diacetylsulfurylamide or N,N'-diethyl-N,N'-dipropionylsulfurylamide;

acylated lactams, such as, for example, acetylcaprolactam, octanoylcaprolactam, benzoylcaprolactam or carbonylbiscaprolactam;

anthranil derivatives, such as, for example, 2-methylanthranil or 2-phenylanthranil;

triacyl cyanurates, e.g. triacetyl cyanurate or tribenzoyl cyanurate;

oxime esters and bisoxime esters, such as, for example, O-acetylacetone oxime or bisisopropyliminocarbonate;

carboxylic anhydrides, e.g. acetic anhydride, benzoic anhydride, m-chlorobenzoic anhydride or phthalic anhydride;

enol esters, such as, for example, isopropenyl acetate;

1,3-diacyl-4,5-diacyloxyimidazolines, e.g. 1,3-diacetyl-4,5-diacetoxyimidazoline;

tetraacetylglycoluril and tetrapropionylglycoluril;

diacylated 2,5-diketopiperazines, e.g. 1,4-diacetyl-2,5-diketopiperazine;

ammonium-substituted nitriles, such as, for example, N-methylmorpholinium acetonitrile methylsulfate;

acylation products of propylenediurea and 2,2-dimethylpropylenediurea, e.g. tetraacetylpropylenediurea;

α-acyloxypolyacylmalonamides, e.g. α-acetoxy-N,N'-diacetylmalonamide;

diacyldioxohexahydro-1,3,5-triazines, e.g. 1,5-diacetyl-2,4-dioxohexahydro-1,3,5-triazine;

benz-(4H)1,3-oxazin-4-ones having alkyl radicals, e.g. methyl, or aromatic radicals, e.g. phenyl, in the 2-position;

cationic nitriles, as described in DE-A-101 48 577.

The described bleaching system comprising bleaches and bleach activators can optionally also comprise bleach catalysts. Examples of suitable bleach catalysts are quaternized imines and sulfonimines, which are described, for example, in U.S. Pat. No. 5,360,569 and EP-A 453 003. Particularly effective bleach catalysts are manganese complexes, which are described, for example, in WO-A 94/21777. Where used, such compounds are incorporated into the detergents in amounts of at most up to 1.5% by weight, in particular up to 0.5% by weight, and in the case of very active manganese complexes, in amounts up to 0.1% by weight. Further suitable bleach catalysts are described in WO 99/19435.

Further bleaching systems based on arylimidoperalkanoic acids which can be used are described in EP-A-0 325 288 and EP-A-0 490 409.

Bleach Stabilizer

These are additives which are able to absorb, bind or complex traces of heavy metals. Examples of additives with a bleach-stabilizing action which can be used according to the invention are polyanionic compounds, such as polyphosphates, polycarboxylates, polyhydroxypolycarboxylates, soluble silicates as completely or partially neutralized alkali metal or alkaline earth metal salts, in particular as neutral Na or Mg salts which are relatively weak bleach stabilizers. Strong bleach stabilizers which can be used according to the invention are, for example, complexing agents, such as ethylenediamine tetraacetate (EDTA), nitrilotriacetic acid (NTA), methylglycinediacetic acid (MGDA), β-alaninediacetic acid (ADA), ethylenediamine N,N'-disuccinate (EDDS) and phosphonates, such as ethylenediaminetetramethylenephosphonate, diethylenetriaminepentamethylenephosphonate or hydroxyethylidene-1,1-diphosphonic acid in the form of the acids or as partially or completely neutralized alkali metal salts. The complexing agents are preferably used in the form of their Na salts.

As well as the described bleaching system comprising bleaches, bleach activators and optionally bleach catalysts, the use of systems with enzymatic peroxide release or of photoactivated bleaching systems is also possible for the detergents according to the invention, see e.g. U.S. Pat. No. 4,033,718.

For a number of uses, it is expedient for the detergents according to the invention to comprise enzymes. Enzymes which are preferably used in detergents are proteases, amylases, lipases and cellulases. Preferred amounts of the enzymes are from 0.1 to 1.5% by weight, particularly preferably 0.2 to 1.0% by weight, of the formulated enzyme. Examples of suitable proteases are Savinase and Esperase. A suitable lipase is e.g. Lipolase. A suitable cellulase is e.g. Celluzym. The use of peroxidases for activating the bleaching system is also possible. It is possible to use individual enzymes or a combination of different enzymes. Where appropriate, the detergent according to the invention can also comprise enzyme stabilizers, e.g. calcium propionate, sodium formate or boric acids or salts thereof, and/or antioxidants.

The constituents of detergents are known in principle to the person skilled in the art. The lists, above and below, of suitable constituents give merely an illustrative selection of the known suitable constituents.

In addition to the main components stated hitherto, the detergents according to the invention can also comprise the following further customary additives in the amounts customary for this purpose:

Known dispersants, such as naphthalenesulfonic acid condensates or polycarboxylates, soil-carrying agents, soil release agents, such as polyether esters, incrustation inhibitors, pH-regulating compounds, such as alkalis or alkali donors (NaOH, KOH, pentasodium metasilicate, sodium carbonate) or acids (hydrochloric acid, phosphoric acid, amidosulfuric acid, citric acid), buffer systems, such as acetate or phosphate buffer, ion exchangers, perfume, dyes, graying inhibitors, optical (fluorescent) brighteners, color-transfer inhibitors, such as, for example, polyvinylpyrrolidone, biocides, such as isothiazolinones or 2-bromo-2-nitro-1,3-propanediol, hydrotropic compounds as solubility promoters or solubilizers, such as cumenesulfonates, toluenesulfonates, short-chain fatty acids, urea, alcohols or phosphoric alkyl/aryl esters, foam regulators for stabilizing or suppressing foam, e.g. silicone oils, skin and corrosion protectants, disinfecting compounds or systems, such as, for example, those which release chlorine or hypochlorous acid, such as dichloroisocyanurate or which contain iodine, thickeners and extenders and formulating agents.

Graying Inhibitors and Soil Release Polymers

Suitable soil release polymers and/or graying inhibitors for detergents are for example:

polyesters of polyethylene oxides with ethylene glycol and/or propylene glycol and aromatic dicarboxylic acids or aromatic and aliphatic dicarboxylic acids;

polyesters of unilaterally terminally capped polyethylene oxides with di- and/or polyhydric alcohols and dicarboxylic acid.

Such polyesters are known, for example from U.S. Pat. No. 3,557,039, GB-A 1 154 730, EP-A-185 427, EP-A-241 984, EP-A-241 985, EP-A-272 033 and U.S. Pat. No. 5,142,020.

Further suitable soil release polymers are amphiphilic graft or copolymers of vinyl and/or acrylic esters onto polyalkylene oxides (cf. U.S. Pat. No. 4,746,456, U.S. Pat. No. 4,846,995, DE-A-37 11 299, U.S. Pat. No. 4,904,408, U.S. Pat. No. 4,846,994 and U.S. Pat. No. 4,849,126) or modified celluloses, such as, for example, methylcellulose, hydroxypropylcellulose or carboxymethylcellulose.

Color Transfer Inhibitors

The color transfer inhibitors used are, for example, homo- and copolymers of vinylpyrrolidone, of vinylimidazole, of vinyloxazolidone and of 4-vinylpyridine N-oxide having molar masses of from 15 000 to 100 000, and crosslinked finely divided polymers based on these monomers. The use mentioned here of such polymers is known, cf. DE-B-22 32 353, DE-A-28 14 287, DE-A-28 14 329 and DE-A-43 16 023.

Suitable polyvinylpyridinebetaines are described, for example in Tai, Formulating Detergents and Personal Care Products, AOCS Press, 2000, page 113.

In addition to the use in detergents and cleaners for domestic textile washing, the detergent compositions which can be used according to the invention can also be used in the field of commercial textile washing and of commercial cleaning. In this field of use, peracetic acid is usually used as bleach, and is added to the wash liquor as an aqueous solution.

Use in Textile Detergents

A typical pulverulent or granular heavy-duty detergent according to the invention may, for example, have the following composition:

0.5 to 50% by weight, preferably 5 to 30% by weight, of at least one anionic and/or nonionic surfactant, including the mixtures according to the invention, 0.5 to 60% by weight, preferably 15 to 40% by weight, of at least one inorganic builder, 0 to 20% by weight, preferably 0.5 to 8% by weight, of at least one organic cobuilder, 2 to 35% by weight, preferably 5 to 30% by weight, of an inorganic bleach, 0.1 to 20% by weight, preferably 0.5 to 10% by weight, of a bleach activator, optionally in a mixture with further bleach activators, 0 to 1% by weight, preferably up to at most 0.5% by weight, of a bleach catalyst, 0 to 5% by weight, preferably 0 to 2.5%, of a polymeric color transfer inhibitor, 0 to 1.5% by weight, preferably 0.1 to 1.0% by weight, of protease, 0 to 1.5% by weight, preferably 0.1 to 1.0% by weight, of lipase, 0 to 1.5% by weight, preferably 0.2 to 1.0% by weight, of a soil release polymer, ad 100% of customary auxiliaries and adjuncts and water.

Inorganic builders preferably used in detergents are sodium carbonate, sodium hydrogencarbonate, zeolite A and P, and amorphous and crystalline Na silicates, and also phyllosilicates.

Organic cobuilders preferably used in detergents are acrylic acid/maleic acid copolymers, acrylic acid/maleic acid/vinyl ester terpolymers and citric acid.

Inorganic bleaches preferably used in detergents are sodium perborate and sodium carbonate perhydrate.

Anionic surfactants preferably used in detergents are linear and slightly branched alkylbenzenesulfonates (LAS), fatty alcohol sulfates/ether sulfates and soaps.

Enzymes preferably used in detergents are protease, lipase, amylase and cellulase. For the commercially available enzymes, amounts of from 0.05 to 2.0% by weight, preferably 0.2 to 1.5% by weight, of the formulated enzyme, are generally added to the detergent. Suitable proteases are, for example, Savinase, Desazym and Esperase. A suitable lipase is, for example, Lipolase. A suitable cellulase is, for example, Celluzym.

Soil release polymers and graying inhibitors preferably used in detergents are graft polymers of vinyl acetate onto polyethylene oxide of molar mass 2500-8000 in the weight ratio 1.2:1 to 3.0:1, polyethylene terephthalates/oxyethylene terephthalates of molar mass 3000 to 25 000 from polyethylene oxides of molar mass 750 to 5000 with terephthalic acid and ethylene oxide and a molar ratio of polyethylene terephthalate to polyoxyethylene terephthalate of from 8:1 to 1:1, and block polycondensates according to DE-A-44 03 866.

Color transfer inhibitors preferably used in detergents are soluble NVP homopolymers and/or vinylpyrrolidone and vinylimidazole copolymers with molar masses greater than 5000.

The detergents are often in solid, pulverulent form, in which case they usually additionally comprise customary extenders, which give them good flowability, dosability and solubility and which prevent caking and dusting, such as sodium sulfate or magnesium sulfate.

The pulverulent or granular detergents according to the invention can comprise up to 60% by weight of inorganic extenders. However, the detergents according to the invention preferably have a low content of extenders and comprise only up to 20% by weight, particularly preferably only up to 8% by weight, of extenders.

The detergents according to the invention can have various bulk densities in the range from 300 to 1200, in particular 500 to 950 g/l. Modern compact detergents usually have high bulk densities and are granular in structure.

Compact or ultracompact detergents and extrudates have a bulk density of >600 g/l. These are becoming more important.

If they are to be used in liquid form, they may be in the form of aqueous microemulsions, emulsions or solutions. In liquid detergents, solvents such as ethanol, isopropanol, 1,2-propylene glycol or butyl glycol can additionally be used.

In the case of gel detergents according to the invention, thickeners, such as, for example, polysaccharides and/or weakly crosslinked polycarboxylates (for example Carbopol® from Goodrich) can additionally be used.

In the case of tablet detergents, tableting auxiliaries, such as, for example, polyethylene glycols with molar masses of >1000 g/mol, polymer dispersions, and tablet disintegrants such as cellulose derivatives, crosslinked polyvinylpyrrolidone, crosslinked polyacrylates or combinations of acids, e.g. citric acid+sodium bicarbonate, to. name but a few, are additionally required.

The present invention further provides for the use of the mixtures in the preparation of detergents.

The invention further provides a washing process using a detergent according to the invention.

The invention is described in more detail by reference to the examples below.

PREPARATION EXAMPLES

The alcohol and KOH (finely powdered) are mixed and dewatered at 80° C. and 40 mbar for 1 hour. The reaction product is placed into an autoclave, the autoclave is rendered inert by flushing twice with nitrogen and is then heated to 120° C. Over the course of 15 minutes, ethylene oxide is metered in to a maximum pressure of 1 bar. This pressure is held for 5 min, then increased by adding ethylene oxide over the course of 60 min to 3 bar, this pressure is held for 5 hours and, finally, the pressure is increased to 6 bar. In the case of the last metered addition, only enough ethylene oxide is added until the amount of ethylene oxide given below is reached. The pressure is then held at 6 bar through the metered addition of nitrogen. After a reaction time of a further 10 hours, the system is left to cool to room temperature and the reaction product is removed. Volatile components are removed on a rotary evaporator at 30 mbar and 80° C.

Example 1

2-Propylheptanol+5 EO 474 g of 2-propylheptanol (3.0 mol), 661 g of ethylene oxide (15.0 mol) and 2.3 g of KOH were used.

Example 2

2-Propylheptanol+7 EO 474 g of 2-propylheptanol (3.0 mol), 925 g of ethylene oxide (21.0 mol) and 2.8 g of KOH were used.

Example 3

2-Propylheptanol+10 EO 474 g of 2-propylheptanol (3.0 mol), 1322 g of ethylene oxide (30.0 mol) and 3.6 g of KOH were used.

Example 4 iso-C13-Alcohol 5 EO 401 g of iso-C13-alcohol (2.0 mol), 441 g of ethylene oxide (10.0 mol) and 1.7 g of KOH were used.

Example 5 iso-C13-Alcohol 7 EO 401 g of iso-C13-alcohol (2.0 mol), 617 g of ethylene oxide (14.0 mol) and 2.0 g of KOH were used.

Example 6 iso-C13-Alcohol 11 EO 401 g of iso-C13-alcohol (2.0 mol), 969 g of ethylene oxide (22.0 mol) and 2.7 g of KOH were used.

Application Examples

| Washing conditions | Primary detergency |
|---|---|
| Machine | Launder-o-meter from Atlas, Chicago USA |
| Wash liquor | 250 ml |
| Wash time | 30 min. at the given temperature (including heating time) |
| Detergent dose | 4.5 g/l |
| Water hardness | 3 mmol/l   Ca:Mg 4:1 |
| Liquor ratio | 1:12.5 |

| Test fabric | | Manufacturer | |
|---|---|---|---|
| wfk 10C | wool grease/pigment on cotton | wfk | Testgewebe GmbH, Brüggen, Germany |
| wfk 10D | skin grease/pigment on cotton | wfk | Testgewebe GmbH, Brüggen, Germany |
| wfk 20D | skin grease/pigment on mixed fabric | wfk | Testgewebe GmbH, Brüggen, Germany |
| wfk 10PF | vegetable fat/pigment on cotton | wfk | Testgewebe GmbH, Brüggen, Germany |
| EMPA 101 | olive oil/soot on cotton | EMPA | Test materials, St. Gallen, Switzerland |

The washed test fabrics are measured using a photometer from Datacolor (Elrepho 2000). The soil removal is given as a percentage. The higher the soil removal, the better the primary detergency.

| Washing formulation | |
|---|---|
| Sodium carbonate | 12% |
| Sodium perborate monohydrate | 14.4% |
| Sodium silicate | 3% |
| Sodium sulfate | 4% |
| Soap | 0.5% |
| AA/MA copolymer 7:3 | 5% |
| TAED | 4% |
| Carboxymethylcellulose | 1.2% |
| Zeolite A | 30% |
| Surfactants according to the invention | as given |
| Water | ad 100% |

R = reflectance value at 460 nm

The results of the washing experiments are summarized in the table below.

TABLE

| Surfactant 1 From Example | Surfactant 2 from Example | Amount of surfactant 1 [%] | Amount of surfactant 2 [%] | Wash temperature | Fabric type wfk 10C Soil removal in % | wfk 10D Soil removal in % | wfk 20 D Soil removal in % | wfk 10 PF Soil removal in % | EMPA 101 Soil removal in % |
|---|---|---|---|---|---|---|---|---|---|
| 1 | — | 6 | — | 25° C. | 5.2 | 0.4 | 4.0 | — | — |
| 1 | 4 | 3 | 3 | 25° C. | — | 19.9 | 26.2 | — | — |
| 1 | 5 | 3 | 3 | 25° C. | 7.7 | 20.4 | 22.5 | — | — |
| 1 | — | 6 | — | 40° C. | 6.1 | 0.4 | 3.5 | 6.9 | 3.3 |
| 1 | 4 | 3 | 3 | 40° C. | 23.2 | 29.5 | 32.5 | 26.3 | 7.7 |
| 1 | 5 | 3 | 3 | 40° C. | 17.6 | 24.6 | 30.8 | — | 11.1 |
| 1 | 6 | 4 | 2 | 40° C. | 25.0 | 30.6 | 31.1 | 28.7 | 6.3 |
| 1 | — | 6 | — | 60° C. | 13.1 | 0.7 | 5.9 | 13.8 | 7.5 |
| 1 | 4 | 3 | 3 | 60° C. | 40.8 | 48.9 | 27.7 | 29.4 | — |
| 1 | 5 | 3 | 3 | 60° C. | 28.1 | 32.2 | 59.5 | — | 11.3 |
| 1 | 6 | 4 | 2 | 60° C. | 23.4 | 40.8 | 31.7 | 40.1 | 16.9 |
| 2 | — | 6 | — | 40° C. | 4.9 | 26.0 | 10.3 | 5.7 | 9.2 |
| 2 | 4 | 3 | 3 | 40° C. | 15.8 | 46.1 | 21.5 | 11.8 | 12.2 |
| 2 | 5 | 3 | 3 | 40° C. | 19.4 | 37.9 | 36.8 | 18.6 | 15.1 |
| 2 | — | 6 | — | 60° C. | 17.9 | 32.0 | 7.7 | 6.9 | 10.7 |
| 2 | 4 | 3 | 3 | 60° C. | 29.9 | 40.8 | 18.5 | 18.8 | 11.6 |
| 2 | 5 | 3 | 3 | 60° C. | 25.6 | 46.6 | 40.0 | 26.4 | 17.4 |
| 3 | — | 6 | — | 40° C. | 7.6 | 2.1 | 1.9 | 7.5 | 7.0 |
| 3 | 4 | 3 | 3 | 40° C. | 15.5 | 19.2 | 16.4 | — | 10.8 |
| 3 | 5 | 3 | 3 | 40° C. | 19.4 | 37.8 | 41.7 | 31.6 | 8.1 |
| 3 | — | 6 | — | 60° C. | 14.7 | 0.3 | 7.2 | 13.5 | 10.8 |
| 3 | 4 | 3 | 3 | 60° C. | 28.5 | 18.8 | 35.6 | — | 21.2 |
| 3 | 5 | 3 | 3 | 60° C. | 25.3 | 40.1 | 34.5 | 30.0 | 17.2 |

As the results summarized in the table show, the use of the alkoxylate mixture according to the invention leads to a considerable improvement in the primary detergency in the detergent.

Example 7

Catalyst Preparation: DMC-Catalyst

In a stirrid tank having a volume of 30 l, equipped a mechanical stirrer, dip pipe for metering, pH-probe head and scattered light probe head, 16000 g aqueous hexa cyano cobaltato acid (cobalt content: 9 g (l) were provided and heated to 50° C. under agitation. Afterwards 9224 g of an aqueous solution of zinc acetate dihydrate (zinc content: 2,6% by weight), which was tempered to 50° C., too, were added under agitation with an agitation power of 0.4 W/l within 15 minutes.

351 g Pluronic® PE 6200 (BASF AG) were added to this precipitation suspension and the mixture is stirred for additional 10 minutes.

Afterwards additional 3690 g of an aqueous solution of zinc acetate dihydrate (zinc content: 2.6% by weight) were added under agitation with an agitation power of 1 W/l within 5 minutes.

The suspension was stirred for two hours. The pH-value dropped during this time from 4.02 to 3.27 and remained constant. The obtained precipitation suspension was filtered off afterwards and the solid residue was washed with six times the amount of water.

The wet solid residue was dried and was dispersed in Tridekanol® using a mill (Spalt-Rotor-Mühle). The obtained suspension has a content of multimetall cyanide of 5% by weight.

2-Propylheptyl alcohol+5 EO, 25 ppm DMC 474 g (3.0 mol) 2-propyl-heptyl alcohol-1 (isomeric mixture of 87% of 2-propyl-heptyl alcohol-1, 11% of 2-propyl-4-methyl heseyl alcohol-1, <1% 2-propyl-5-methyl hexyl alcohol-1) and 0.567 g of a suspension of double metal cyanide with a content of 5% in an isomeric mixture of 2-propyl heptyl alcohol (25 ppm in respect of the product) as catalyst were dehydrated at a temperature of 80° C. and at about 1 mbar, added to a 2 1-autoclave, flushed three times with nitrogen and heated to 120° C. afterwards. After reaching this temperature 660 g (15 mol) ethylenoxide were added continuously at a pressure of 0.1 to 3.7 bar (gradient of pressure 6 bar/90 min). After completion of the addition of the oxide the reaction mixture was left to react (20 minutes), was cooled to 80° C. afterwards, flushed three times with nitrogen and emptied. The obtained product was degassed at 80° C. under reduced pressure (<30 mbar) at the rotary evaporator (reaction product has not been filtered).

Example 8

2-Propylheptyl Alcohol+8 EO, 25 ppm DMC

Reaction was conducted with 474 g (3.0 mol) 2-propyl-heptyl alcohol isomeric mixture, 0.77 g of a suspension of double metalcyanide and 1060 g (24.0 mol) ethylene oxide. The products obtained according to examples 7 and 8 were tested according to the products obtained according to examples 1 to 6.

The invention claimed is:

1. An alkoxylate mixture comprising 10 to 90% by weight of at least one alkoxylate of the formula (I)

$$C_5H_{11}CH(C_3H_7)CH_2O(A)_xH \qquad (I)$$

wherein
A is ethyleneoxy,
x is a number in the range from 1 to 20,
wherein 70 to 99% by weight of the alkoxylate A1 of formula (I) have an n-$C_5H_{11}$ group for the $C_5H_{11}$ group of formula (I) and 1 to 30% by weight of the alkoxylate A2 of formula (I) have a $C_2H_5CH(CH_3)CH_2$ and/or a $CH_3CH(CH_3)CH_2CH_2$ group for the $C_5H_{11}$ group of formula (I), and
10 to 90% by weight, of at least one alkoxylate of the formula (II)

$$C_mH_{2m+1}O(A)_v(B)_wH \qquad (II)$$

wherein
A is ethyleneoxy,
B is $C_3$-$C_{10}$-alkyleneoxy or mixtures thereof,
where groups A and B may be present, randomly distributed, alternately, or in the form of two or more blocks in any order,
m is an integer in the range from 12 to 24,
v is a number in the range from 1 to 50,
w is a number in the range from 0 to 10.

2. The mixture as claimed in claim 1, wherein, in the alkoxylate of the formula (II), m is an integer in the range from 12 to 18.

3. The mixture as claimed in claim 1, wherein, in the alkoxylate of the formula (I), x is a number in the range from 3 to 12 and in the general formula (II), v is a number in the range from 3 to 15 and w has the value 0.

4. A process for the preparation of the alkoxylate mixtures, as claimed in claim 1, comprising, reacting alkanols of the formula $C_mH_{2m+1}OH$ and 2-propyl heptyl alcohol, with the given meaning for m, with $C_{2-5}$-alkylene oxides, under alkoxylation conditions, and mixing them together, before, or after, alkoxylation, or after partial alkoxylation, and wherein the alkoxylation may be conducted in the presence of a double metal cyanide compound as catalyst.

5. A detergent or cleaner comprising an alkoxylate mixture as claimed in claim 1, and one or more additives.

6. A detergent or cleaner, comprising an alkoxylate mixture, as claimed in claim 1, wherein the alkoxylate mixture is present in an amount of from 0.01 to 80% by weight, based on the detergent or cleaner.

7. A method of washing or cleaning textiles, comprising applying the detergent or cleaner, as claimed in claim 5, to one or more textiles.

8. The mixture as claimed in claim 1, wherein the alkoxylate of formula (I) consists of the alkoxylate A1 and A2.

* * * * *